United States Patent
Koehler et al.

(10) Patent No.: US 9,458,511 B2
(45) Date of Patent: Oct. 4, 2016

(54) MULTIPLEXED DIGITAL ASSAY FOR VARIANT AND NORMAL FORMS OF A GENE OF INTEREST

(71) Applicant: Bio-Rad Laboratories, Inc., Hercules, CA (US)

(72) Inventors: Ryan T. Koehler, West Linn, OR (US); Svilen S. Tzonev, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 267 days.

(21) Appl. No.: 14/215,516

(22) Filed: Mar. 17, 2014

(65) Prior Publication Data

US 2014/0274799 A1    Sep. 18, 2014

Related U.S. Application Data

(60) Provisional application No. 61/789,712, filed on Mar. 15, 2013.

(51) Int. Cl.
*C12Q 1/68* (2006.01)
*C12P 19/34* (2006.01)

(52) U.S. Cl.
CPC ............ *C12Q 1/6886* (2013.01); *C12Q 1/686* (2013.01); *C12Q 1/6851* (2013.01); *C12Q 2600/156* (2013.01)

(58) Field of Classification Search
None
See application file for complete search history.

(56) References Cited

U.S. PATENT DOCUMENTS

2009/0069194 A1* 3/2009 Ramakrishnan ..... C12Q 1/6851
506/9
2012/0302448 A1    11/2012  Hutchison et al.
2012/0322058 A1    12/2012  Regan et al.

OTHER PUBLICATIONS

Nicole L. Solimini et al., "Recurrent Hemizygous Deletions in Cancers May Optimize Proliferative Potential", Science Magazine, vol. 337, Jul. 6, 2012, 6 pages.
Lee W. Young, Authorized Officer, U.S. Commissioner for Patents, "International Search Report" in connection with related PCT Patent App. No. PCT/US2014/030237, dated Oct. 31, 2014, 4 pages.
Lee W. Young, Authorized Officer, U.S. Commissioner for Patents, "Written Opinion of the International Searching Authority" in connection with related PCT Patent App. No. PCT/US2014/030237, dated Oct. 31, 2014, 12 pages.

* cited by examiner

*Primary Examiner* — David Thomas
(74) *Attorney, Agent, or Firm* — Kolisch Hartwell, P.C.

(57) ABSTRACT

System, including methods, apparatus, and compositions, for performing a multiplexed digital assay of at least three targets. In an exemplary method, partitions may be formed each including a portion of a same sample. The sample may include a first target that is a reference sequence, a second target that is a variant sequence from a gene of interest, and a third target that is a normal sequence from the gene of interest. The target may be amplified in the partitions and amplification data may be collected. A level of the second target may be determined. A copy number of the third target may be determined from a level of the first target and a level of the third target.

20 Claims, 7 Drawing Sheets

MULTIPLEXED DIGITAL ASSAY FOR VARIANT AND NORMAL FORMS OF A GENE OF INTEREST

CROSS-REFERENCE TO PRIORITY APPLICATION

This application is based upon and claims the benefit under 35 U.S.C. §119(e) of U.S. Provisional Patent Application Ser. No. 61/789,712, filed Mar. 15, 2013, which is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2013/0040841 A1, published Feb. 14, 2013; U.S. Patent Application Publication No. 2013/0045875 A1, published Feb. 21, 2013; U.S. patent application Ser. No. 14/099,750, filed Dec. 6, 2013; U.S. patent application Ser. No. 14/171,754, filed Feb. 3, 2014; U.S. patent application Ser. No. 14/171,761, filed Feb. 3, 2014; U.S. patent application Ser. No. 14/191,295, filed Feb. 26, 2014; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized to determine the concentration of the analyte in the partitions, such as with Poisson statistics.

Digital assays frequently rely on amplification of a nucleic acid target in partitions to enable detection of a single copy of an analyte. Amplification may be conducted via the polymerase chain reaction (PCR), to achieve a digital PCR assay. The target amplified may be the analyte itself or a surrogate for the analyte generated before or after formation of the partitions. Amplification of the target can be detected optically from a fluorescent probe included in the reaction. In particular, the probe can include a fluorophore that provides a fluorescence signal indicating whether or not the target has been amplified.

Digital assays can produce populations of target-positive partitions that are not resolved from each other in the data. New approaches are needed to determine target levels when such populations exhibit overlap.

SUMMARY

The present disclosure provides a system, including methods, apparatus, and compositions, for performing a multiplexed digital assay of at least three targets. In an exemplary method, partitions may be formed each including a portion of a same sample. The sample may include a first target that is a reference sequence, a second target that is a variant sequence from a gene of interest, and a third target that is a normal sequence from the gene of interest. The target may be amplified in the partitions and amplification data may be collected. A level of the second target may be determined. A copy number of the third target may be determined from a level of the first target and a level of the third target.

3-7 after target amplification in the partitions, in accordance with aspects of the present disclosure.

Figure 8:
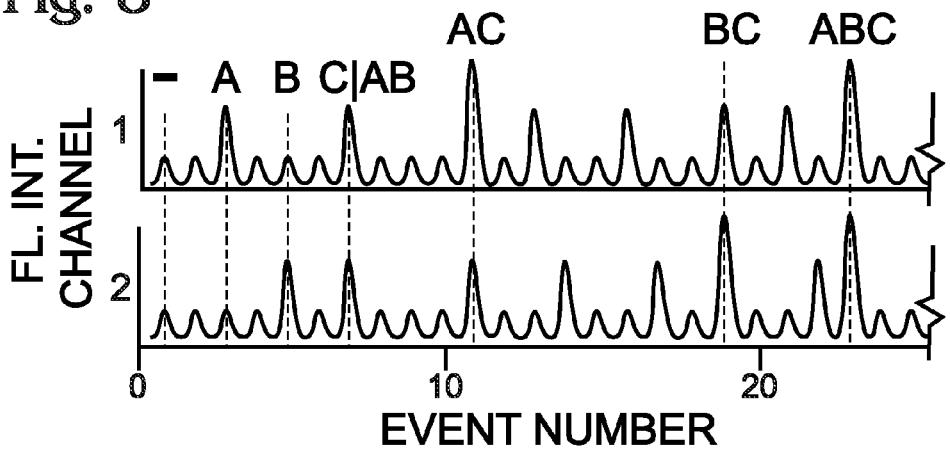
FIG. 8 is a pair of fragmentary graphs illustrating a portion of exemplary fluorescence intensity data that may be collected from partitions formed according to any of FIGS.
Figure 9:
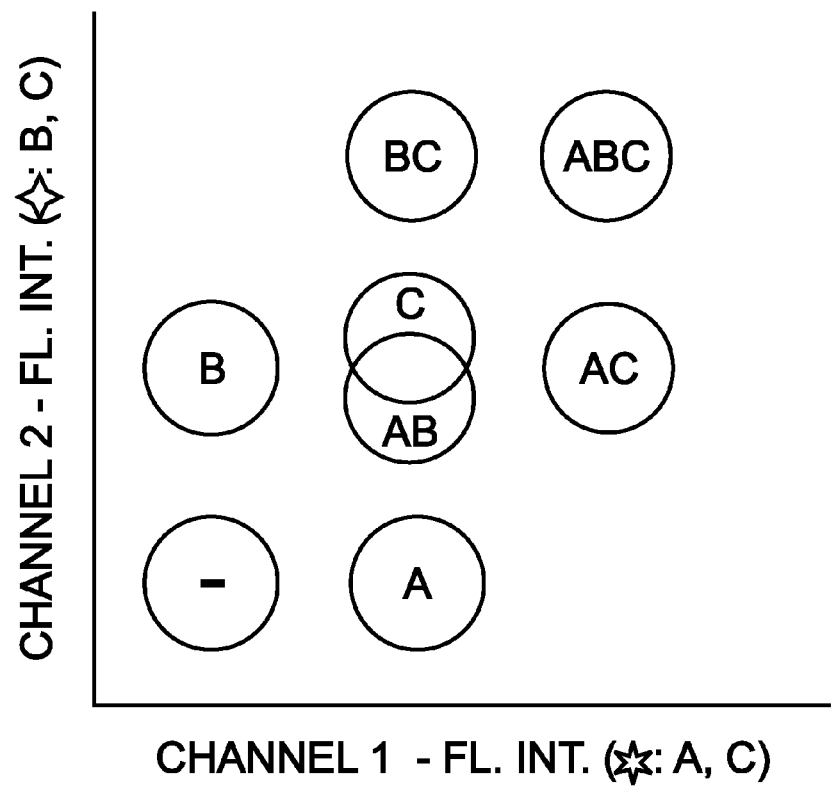

FIG. 9 is a schematic view of a scatter plot of the fluorescence data of FIG. 8 with each partition (or "event") being graphed as a data point according to fluorescence amplitude detected in each channel for the partition, and with each cluster or population of partitions/data points being represented schematically by a circle, in accordance with aspects of the present disclosure.

Figure 10:
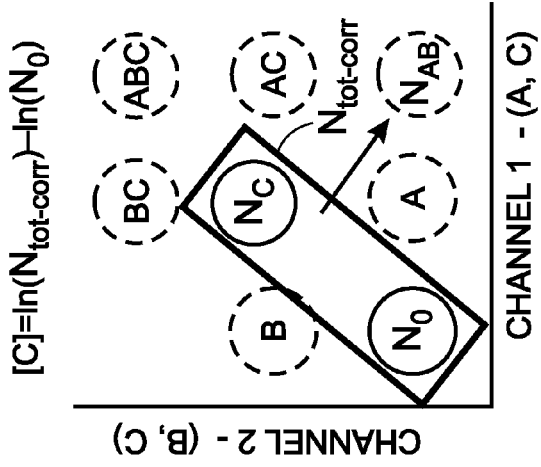

FIG. 10 shows the scatter plot of FIG. 9 in a modified form to illustrate an exemplary approach for calculating the concentration of target A from only a subset of the data, namely, a partition count for completely negative partitions and a partition count for partitions positive only for target A, in accordance with aspects of the present disclosure.

Figure 11:
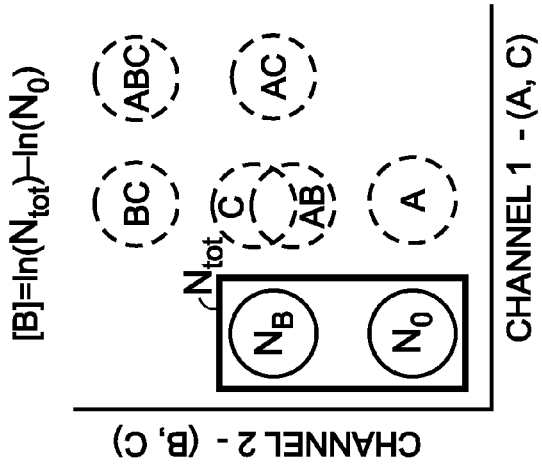

FIG. 11 shows the scatter plot of FIG. 9 in a modified form to illustrate an exemplary approach for calculating the concentration of target B from only a subset of the data, namely, a partition count for completely negative partitions and a partition count for partitions positive only for target B, in accordance with aspects of the present disclosure.

Figure 12:
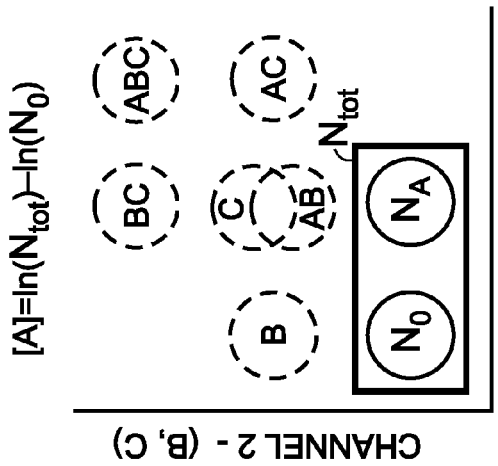

FIG. 12 shows the scatter plot of FIG. 9 in a modified form to illustrate an approach for calculating the concentration of target C from only a subset of the data, namely, a partition count for completely negative partitions and a partition count for a mixed cluster of C-positive partitions overlapped with AB-positive partitions and adjusted to decrease the partition count by a calculated number of AB-positive partitions in the cluster, in accordance with aspects of the present disclosure.

Figure 13:
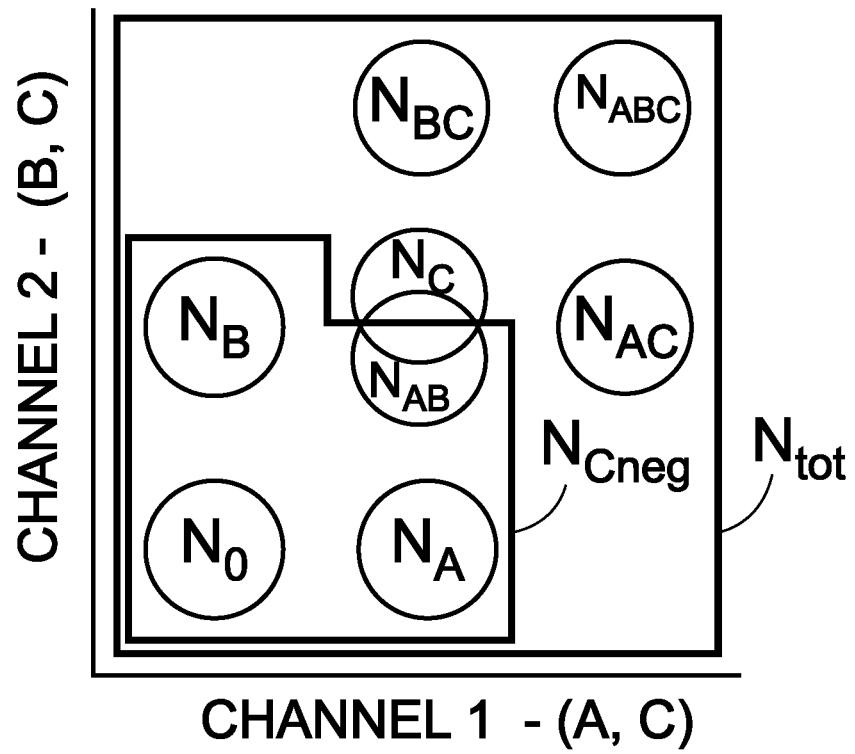

FIG. 13 shows the scatter plot of FIG. 9 in a modified form to illustrate another exemplary approach for calculating the concentration of target C, using data from all of the partitions, namely, a calculated number of C-negative partitions and a total count of all partitions, in accordance with aspects of the present disclosure.

Figure 14:
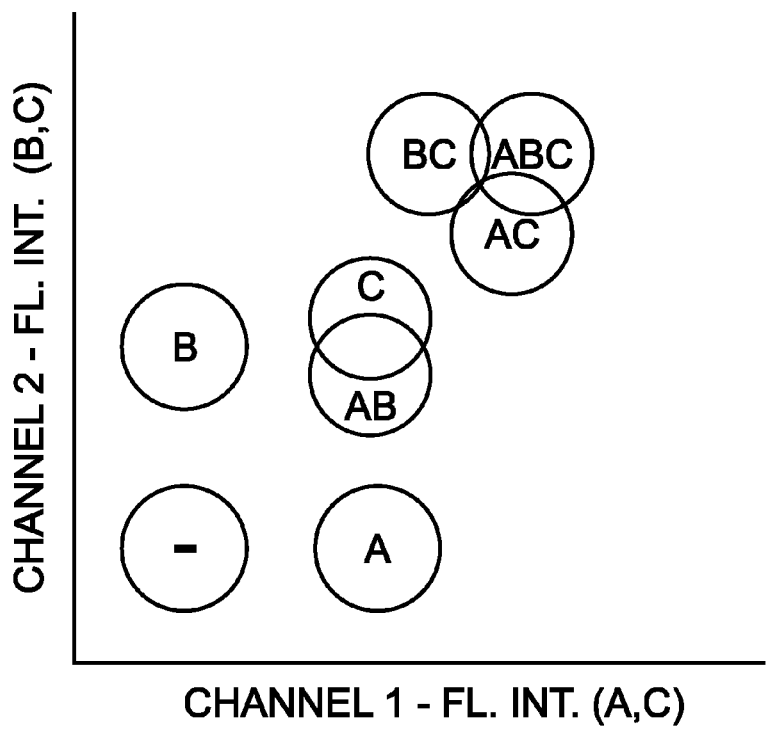

FIG. 14 is another exemplary schematic view of a scatter plot that may result from the fluorescence data of FIG. 8 with each partition (or "event") being graphed as a data point according to fluorescence amplitude detected in each channel for the partition, and with each cluster or population of partitions/data points being represented schematically by a circle, in accordance with aspects of the present disclosure.

Figure 15:
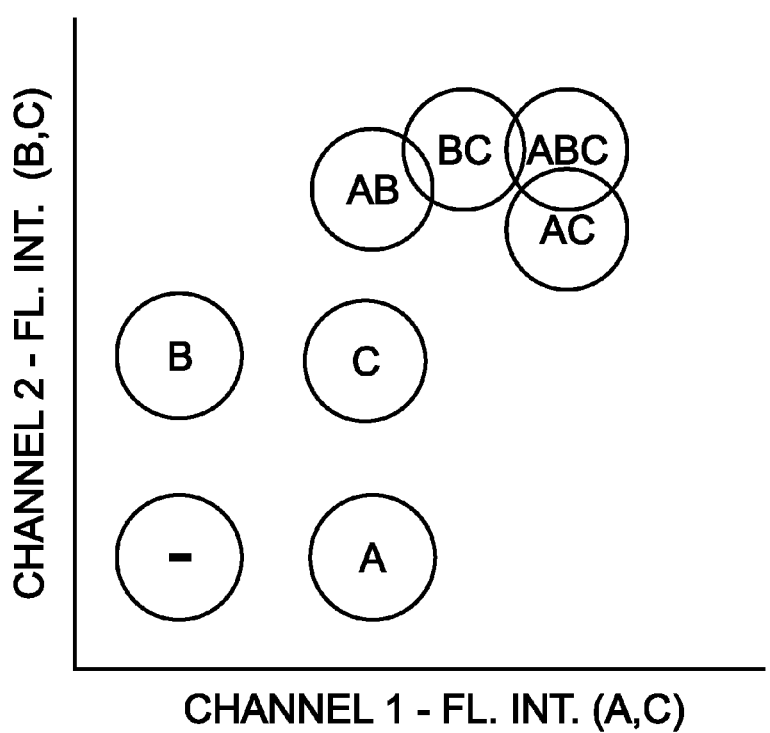

FIG. 15 is still another exemplary schematic view of a scatter plot that may result from the fluorescence data of FIG. 8 with each partition (or "event") being graphed as a data point according to fluorescence amplitude detected in each channel for the partition, and with each cluster or population of partitions/data points being represented schematically by a circle, in accordance with aspects of the present disclosure.

DETAILED DESCRIPTION

The present disclosure provides a system, including methods, apparatus, and compositions, for performing a multiplexed digital assay of at least three targets. In an exemplary method, partitions may be formed each including a portion of a same sample. The sample may include a first target that is a reference sequence, a second target that is a variant sequence from a gene of interest, and a third target that is a normal sequence from the gene of interest. The target may be amplified in the partitions and amplification data may be collected. A level of the second target may be determined. A copy number of the third target may be determined from a level of the first target and a level of the third target.

Another exemplary method of performing a multiplexed digital assay is provided. In the method, partitions may be formed each including a portion of a same fluid volume that contains a first target, a second target, and a third target. The first target, the second target, and the third target may be amplified in the partitions. Data may be collected from a plurality of the partitions for amplification of each of the targets. In the data, an alpha population of partitions each positive for both of the first and second targets may at least partially overlap a beta population of partitions positive for only the third target. A level of the first target and a level of the second target may be determined from only a portion of the data that excludes both the alpha population and the beta population. A number of partitions in the alpha population may be determined. A level of the third target may be determined based in part on the number of partitions in the alpha population.

Further aspects of the present disclosure are presented in the following sections: (I) system overview, and (II) examples.

I. SYSTEM OVERVIEW

This section provides an overview of exemplary methods and apparatus for performing multiplexed digital assays with overlapping target-positive populations.

Figure 1:
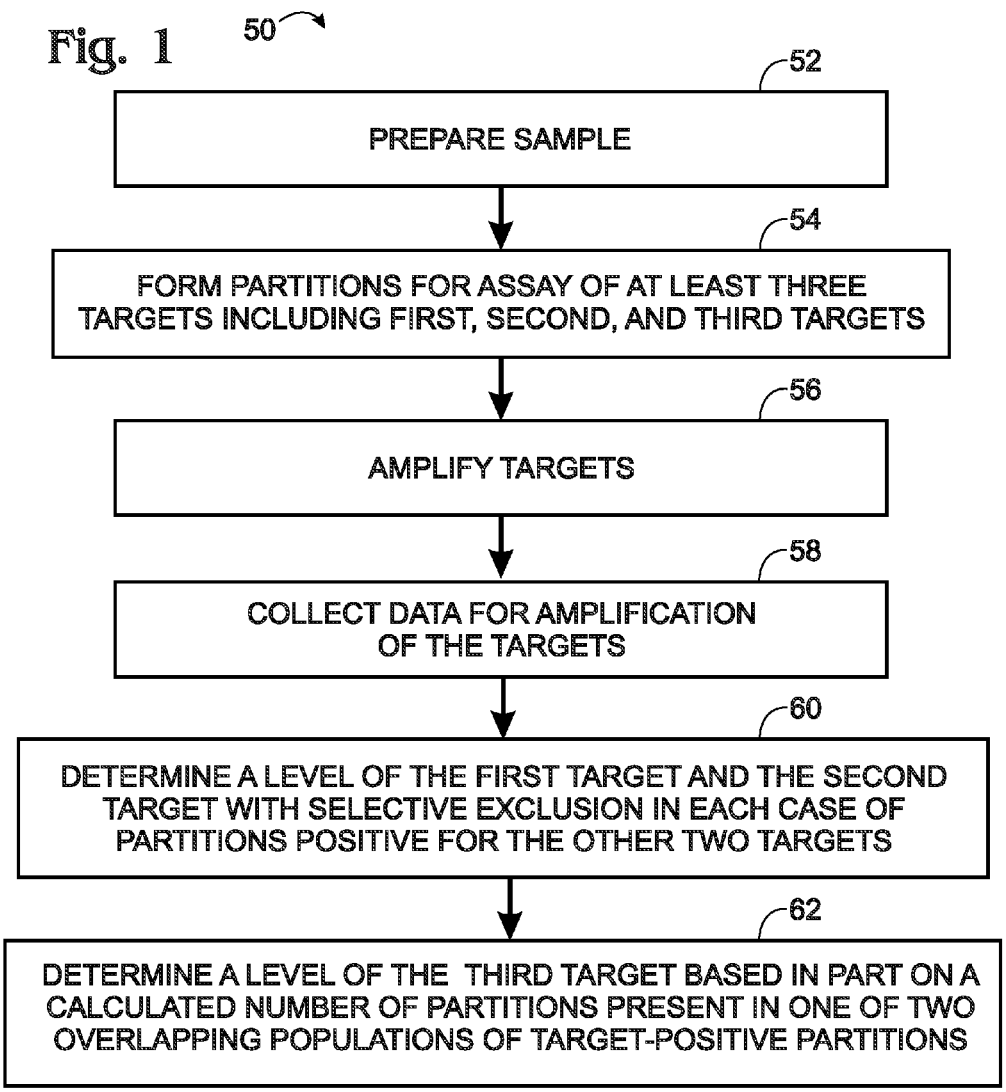
FIG. 1 is a flowchart of an exemplary method of performing a multiplexed digital assay with unresolved target-positive populations, in accordance with aspects of the present disclosure.

FIG. 1 shows a flowchart of an exemplary method 50 of performing a multiplexed digital assay with unresolved target populations. The steps presented for method 50 may be performed in any suitable order and in any suitable combination. Furthermore, the steps may be combined with and/or modified by any other suitable steps, aspects, and/or features of the present disclosure, including those described in the patent documents listed above under Cross-References, which are incorporated herein by reference.

Sample Preparation.

A sample may be prepared for the assay, indicated at 52. Preparation of the sample may include any suitable manipulation of the sample, such as collection, dilution, concentration, purification, lyophilization, freezing, extraction, restriction-enzyme digestion, shearing, combination with one or more assay reagents to form a mixture (also termed a sample-containing mixture or fluid, a bulk phase, or a reaction mixture), performance of at least one preliminary reaction to prepare the sample for one or more reactions in the assay, or any combination thereof, among others. The preparation may isolate nucleic acid that includes copies of one or more nucleic acid targets, and/or may modify and/or fragment the nucleic acid. Preparation of the sample may include rendering the sample competent for subsequent performance of one or more reactions, such as one or more enzyme-catalyzed reactions and/or binding reactions.

In some embodiments, preparation of the sample may include combining the sample with reagents to produce a sample-containing mixture for performance of at least three different assays within the same multiplexed assay, such as at least three amplification assays to assay at least three targets. The reagents thus may include primers for amplification of each target and one or more detectable reporters to report whether or not amplification of each target occurred (e.g., above a threshold level or within a range). Reagents for amplification may include any combination of primers for targets, dNTPs and/or NTPs, at least one enzyme (e.g., a polymerase, a ligase, a reverse transcriptase, a restriction enzyme, or a combination thereof, among others, each of which may or may not be heat-stable), and/or the like. Accordingly, the mixture may have a complete set of reagents for (i.e., may be competent for) amplification of each target under suitable environmental conditions (e.g., incubation at an elevated temperature or modulation of temperature (such as by thermocycling)). The mixture may be capable of amplification of each of one or more targets, if present, in the sample (or portion thereof). Reagents for reporting may include at least one generic reporter (interchangeably termed a nonspecific reporter) and/or at least one specific reporter. The generic reporter may be sensitive to amplification of each target and each specific reporter may be specifically sensitive to amplification of only a subset of the targets, such as only one of the targets. The mixture may or may not include a different reporter for each target to be assayed. Preparation of the mixture may render the sample capable of reporting, or being analyzed for, whether or not a reaction, such as amplification, has occurred, on a target-by-target basis, and optionally the extent of any such reaction. The reporters each may be a probe that includes a specific binding partner (e.g., an oligonucleotide) for a nucleic acid sequence. The probe may include a luminophore (e.g., a photoluminescent moiety), such as a fluorophore. Alternatively, or in addition, at least one generic reporter may be utilized. In some cases, the same generic reporter may report amplification of each target.

The term "luminescence" means emission of light that cannot be attributed merely to the temperature of the emitting body. Exemplary forms of luminescence include photoluminescence, chemiluminescence, electroluminescence, or the like. A "luminophore" is any atom or associated group of atoms capable of luminescence. Photoluminescence is any luminescence produced in response to irradiation with excitation light and includes fluorescence, phosphorescence, etc. Accordingly, a luminophore may be a fluorophore or a phosphor, among others.

Each target may be a nucleotide sequence. The target may be described as a target sequence (of nucleotides). The target, if nucleic acid, may be single-stranded or double-stranded, among others. A nucleic acid target may be provided by a template, with the target forming at least a portion or all of the template. The target may correspond to an amplicon produced by amplification of the target. The amplicon may be single-stranded or double-stranded, among others. In some cases, the target may be or correspond to an analyte that is not nucleic acid, such as a small molecule, a peptide, a polypeptide/protein, a lipid, an amino acid, an ion, a macromolecular complex, a biological particle (a cell, virion, organelle, etc.), or the like.

Providing Partitions.

Partitions for the assay may be provided, indicated at 54. Each partition may include a portion of a same mixture. In some cases, the portion may constitute the entire partition. The mixture may contain each target (e.g., provided by a same sample), each reporter, and/or one or more amplification reagents (e.g., a complete set of reagents for amplification of each target). Accordingly, the partitions, collectively, may contain a plurality of targets and each partition may contain the same reporter(s). The targets may include at least one reference target and a pair of targets for a gene of interest, such as a variant sequence and a normal sequence for the gene. The variant sequence and the normal sequence may represent genomic sequences or cDNA/RNA sequences, among others, from the gene.

The partitions when provided (e.g., when formed) may contain each target at "partial occupancy," which means that each partition of only a subset of the partitions contains at least one copy of each target to be assayed. For example, with a multiplexed assay performed on a first target, a second target, and a third target, only a first subset of the partitions contains the first target, only a second subset of the partitions contains the second target, and only a third subset of the partitions contains the third target. The subsets are generally different, unless a pair of the targets are fully associated with and/or linked to each other when the partitions are formed. In some cases, two or more of the targets may be present together in each partition of another subset of the partitions. Accordingly, with partial occupancy, one or more (e.g., a plurality) of the partitions contain no copies of the first target, one or more (e.g., a plurality) of the partitions may contain a single copy (only one copy) of the first target, and, optionally, yet one or more of the partitions (e.g., the rest of the partitions) may contain two or more copies of the first target. The same holds for the second target and the third target.

The term "partial occupancy" is not restricted to the case where there is no more than one copy of a particular target in any partition. Partitions containing a target at partial occupancy may, for example, contain an average of more than, or less than, about one copy, two copies, or three copies, among others, of the target per partition when the partitions are provided or formed. Copies of a target may have a random distribution among the partitions, which may be described as a Poisson distribution. In some cases, a significant number of the partitions (e.g., at least about 1%, 2%, 5%, 10%, or 20%, among others, of the partitions) may contain a copy of each of at least two targets, and/or a plurality of the partitions each may contain at least one copy of all targets.

The partitions may be formed by distributing or separating portions of a sample-containing bulk phase into partitions. Any suitable fraction including up to all of the bulk phase may be distributed to the partitions. Each partition may be and/or include a fluid volume that is isolated from fluid volumes of other partitions. The partitions may be isolated from one another by a fluid/liquid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with at least one droplet generator, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 mL, or less than about 100, 10, or 1 µL, among others.

Partitions competent for amplification of each target may be formed directly from a bulk phase containing the template, or may be formed in multiple steps. In some cases, the step of forming partitions may include dividing a bulk phase into isolated fluid volumes (such as droplets) containing each of the targets at partial occupancy. The fluid volumes may be the partitions themselves or may contribute to the partitions. For example, the fluid volumes may be a first set of fluid volumes, and the step of forming partitions may include merging individual fluid volumes of the first set with individual fluid volumes of a second set. The second set may include one or more reagents for amplification of one or more of the targets, such as at least one primer for amplification of at least one of the targets, primers for all of the targets, or the like. The step of merging may include fusing fluid volumes of the first set individually with fluid volumes of the second set, such as fusing droplets containing the target with droplets containing primers for amplification of one or more targets. Alternatively, the step of merging may be performed by combining fluid volumes with a fluid dispenser.

Any pair of the targets may or may not be associated with each other when the partitions are formed. Associated targets co-localize non-randomly to the same partitions, according to the degree of association. For example, the pair of targets may be associated by being present together in or on the same biological particle (e.g., the same biological cell, virion, subcellular organelle, etc.). As another example, the pair of targets may be linked, that is, connected to each other covalently and/or by direct or indirect non-covalent interaction, such as by base pairing, among others. A pair of associated copies of a pair of associated targets remain proximate each other in a sample when partitions are formed and thus distribute to the same partition. The associated targets may have any suitable degree of association and/or linkage of at least about 10%, 25%, 50%, 80%, 90%, or about 100% in the sample before and/or during partition formation. The degree of association/linkage of targets may be known a priori or tested. The degree of association indicates a percentage of the targets that are connected to each other, confined to the same compartment (e.g., the same cell) within the sample, and/or the frequency with which the targets distribute together to the same partitions, after correction for co-localization by chance. Targets that occupy the same partition, whether due to a physical connection during partition formation or due to chance, may be described as being co-localized or coincident in the partition. Targets that have a high degree of association are co-localized to the same partitions at a corresponding high frequency, whether the targets are abundant or rare in the sample. For example, targets that have 90% association should co-localize in at least 90% of the partitions that contain at least one of the targets. In contrast, targets that have no association should co-localize according to the product of the probabilities of finding each target in a given partition, which varies with the concentration of the targets.

The partitions may be configured to perform at least three target assays. In some cases, a pair of the targets may be linked. If linked, the linked targets may represent any suitable connected and/or overlapping pair of regions of the same template. The regions may be spaced from each other along the template, such as separated by at least 50, 100, 200, or 400 nucleotides/base pairs, among others. In some cases, the regions may be separated by a number of nucleotides greater than the length of each region. In some cases, the regions may overlap one another by any suitable number of nucleotides, such as less than twenty, less than ten, or the like. In some embodiments, the regions may overlap at a site of allelic variation. Alternatively, or in addition, each region may be strand-specific, with one of the regions representing one strand of the template and the other region representing the other strand of the template. The strand-specific regions may or may not overlap each other along a template.

Target Amplification.

The targets may be amplified in the partitions, indicated at 56. Amplification of each target may occur selectively (and/or substantially) in only a subset of the partitions, such as less than about three-fourths, one-half, one-fourth, or one-tenth of the partitions, among others. Amplification of each target may occur selectively in partitions containing at least one copy of the target e.g., containing at least one copy of a template that includes the target). Amplification may be linear or exponential, among others.

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature, for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Data Collection.

Amplification data may be collected, indicated at 58. The data may be collected by detecting light from individual partitions. The light may or may not be emitted in response to irradiation of the partitions with excitation light. The data may be collected for emission of light from the partitions in only one wavelength regime (one optical channel), at least two wavelength regimes (e.g., two optical channels), or the like.

Data may be collected from the reporters in the partitions. The partitions may contain only one reporter or a plurality of different reporters having any suitable structure and characteristics. Each reporter may be a specific reporter (e.g., a probe) or a generic reporter (e.g., an intercalating dye). In some cases, at least one specific reporter may report on the occurrence of only one particular reaction and/or only one target in a multiplexed assay. In other cases, a specific reporter may report on the occurrence of two or more reactions and/or two or more targets. Each reporter may be termed a binding partner, a reaction reporter, and/or an amplification reporter.

A specific reporter binds with substantial specificity to a partner (e.g., a target and/or an amplicon), based on an identity of the partner, to the substantial exclusion of other structurally different substances belonging to the same class as the partner. For example, each specific reporter may bind to a particular sequence or site, to the substantial exclusion of other sequences or sites. The specific reporter may include or be a probe including at least one sequence-specific binding partner for nucleic acid (e.g., at least one oligonucleotide) that binds specifically to a complementary nucleotide sequence present in a target and/or an amplicon corresponding to the target. The probe may include a label attached (e.g., covalently attached or bound noncovalently, among others) to a nucleic acid or an aptamer, among others. The label may be optically detectable directly or indirectly. Accordingly, the label may be a luminophore (such as a photoluminescent moiety (e.g., a fluorophore or phosphor)), an enzyme (e.g., a peroxidase, beta-galactosidase, alkaline phosphatase, phosphodiesterase, or the like), a member of a specific binding pair (e.g., biotin or avidin/streptavidin), or an epitope tag, among others. A probe including a luminophore may or may not also include an energy transfer partner for the luminophore, such as a quencher or another luminophore (e.g., to produce luminescence resonance energy transfer (e.g., FRET)). The probe may or may not also function as a primer that is extended in the assay. Exemplary labeled probes include TaqMan® probes, Scorpion® probes/primers, Eclipse® probes, Amplifluor® probes, molecular beacon probes, Lux® primers, proximity-dependent pairs of hybridization probes that exhibit FRET when bound adjacent one another on an amplicon, QZyme® primers, or the like.

The specific reporter may have distinct forms or states. The specific reporter may have an initial/intact form or state and one or more degraded/modified forms or states. The one or more degraded/modified forms or states may be produced from the initial/intact form during amplification of at least one target. The forms or states may be distinguishable optically. For example, the degraded/modified form may be more or less photoluminescent than the initial/intact form.

A nonspecific reporter (interchangeably termed a generic reporter) binds without substantial specificity to a partner (e.g., a target and/or an amplicon), such that other structurally different substances belonging to the same class as the partner (e.g., other amplicons of unrelated sequence) can also be bound by the nonspecific reporter. Nonspecific binding by the nonspecific reporter may not depend on a unique feature of the arrangement of atoms of one or both of the reporter and the partner (e.g., a target and/or amplicon). Multiple copies of the nonspecific reporter may be capable of binding to a single copy of a target/amplicon, for example, with the number of copies bound being related directly, such as proportional, to the amount or length of the target/amplicon. For example, the nonspecific reporter may be a photoluminescent dye that binds to nucleic acid relatively nonspecifically. The dye may not be attached to or include a nucleic acid or aptamer that confers substantial sequence binding specificity.

The dye may be a major groove binder, a minor groove binder, an intercalator, or an external binder, among others. The dye may bind preferentially to double-stranded relative to single-stranded nucleic acid and/or may exhibit a greater change in a photoluminescence characteristic (e.g., emission intensity) when bound to double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

R targets may be assayed in a multiplexed assay, and the data may be collected in less than R optical channels. In other words, the number (R) of targets assayed may be greater than the number of optical channels used for detecting the presence of the targets. In some cases, the data may be collected in only one or two optical channels, or in at least two, three, or more optical channels, among others. In some cases, data may be collected from the same number of optical channels as targets in the assay. An optical channel interchangeably may be termed a detection channel.

An optical channel may represent a particular detection regime with which light is detected. The detection regime may be characterized by a spectral content (i.e., a wavelength regime) for detection of light. If excitation light is used in the detection regime to induce light emission, the detection regime may be characterized by a spectral content (a wavelength(s) or waveband(s)) for illumination with excitation light and/or a time interval during which light emission is detected with respect to each light pulse, if any. Accordingly, optical channels that are different from each other may differ with respect to the spectral content (wavelength(s)/waveband(s)) of excitation light, if any, with respect to the spectral content (wavelength(s)/waveband(s)) of light that is detected, and/or with respect to the time interval during which light is detected relative to each pulse of excitation light, if any, among others.

Data collection, also called signal detection, may include generating one or more signals representative of detected light. Each signal may represent an aspect of light, such as the intensity of the light, detected in the same optical channel from one or more reporters for two or more distinct targets. The signals optionally may include data collected in two or more different optical channels (e.g., at different wavelengths and/or different wavelength ranges (wavebands) and/or color regimes) from reporters for the same and/or different targets). The light detected from each reporter may be light emitted from a luminophore (e.g., a fluorophore). The light detected in a given channel may be detected such that light from different reporters is summed or accumulated without attribution to a particular reporter. Thus, the signal for a given channel may be a composite signal that represents two, three, four, or more reporters and/or assays and two, three, four, or more targets.

The signal(s) may be created based on detected light emitted from one or more reporters in the partitions. The one or more reporters may report whether at least one of two or more particular amplification reactions represented by the signal has occurred in a partition and thus whether at least one copy of at least one of two or more particular targets corresponding to the two or more particular amplification reactions is present in the partition. The level or amplitude of the signal corresponding to the reporters may be analyzed to determine whether or not at least one of the particular amplification reactions has occurred and at least one copy of one of the particular targets is present. The level or amplitude of the signal may vary among the partitions according to whether at least one of the particular amplification reactions occurred or did not occur and at least one of the particular targets is present or absent in each partition. For example, a partition testing positive for a particular target may produce a signal level (interchangeably termed a signal amplitude) that is above a given threshold(s) and/or within a given range(s). Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

Data may be collected from a plurality of the partitions (i.e., only a subset or all of the partitions) under any suitable conditions. All of the data may be collected at about the same temperature from the plurality of partitions, at a temperature that is below a melting temperature of each amplicon, and/or below about 50 degrees Celsius, among others. The amplification data may be collected after an endpoint of amplification has been reached for at least one of the targets or each target.

A presence or absence of each target may be determined (interchangeably termed detected) for each of a plurality of the partitions based on the data collected. A presence of a particular target may be detected in a given partition when at least one copy of the target is present in the partition. The partition can be classified as positive for the target. An absence of the particular target may be detected when no copy of the target is present in the given partition. The partition can be classified as negative for the target.

Population Identification.

Partition populations may be identified from the data. The populations may include a population that tests negative for each of the targets, populations testing positive for only one of the targets (single positives), populations testing positive for only a pair of the targets (double positives), and/or a population testing positive for three of the targets (triple positive), among others. Each population (or two or more overlapping populations) may produce a cluster of data points in the data. Identification may be performed by a data processor using an algorithm (e.g., an algorithm that identifies patterns (e.g., signal clusters) in the data), by a user, or a combination thereof. In some cases, a data processor may produce and output (e.g., display) a plot of the collected data (e.g., a 2-D scatter plot or histogram, or, with three or more optical channels for detection, two or more 2-D scatter plots or histograms with different pairs of axes, etc.). The user then may define a boundary of each population/cluster based on the plot(s), e.g., through a graphical user interface to define population/cluster boundaries, and/or by inputting values (e.g., representing signal amplitude thresholds/ranges) to define a boundary for each population/cluster. Each population/cluster boundary may be defined by one or more thresholds or ranges of values, a geometrical shape that surrounds the population/cluster (e.g., a polygon, ellipse, etc.), or the like. In some cases, at least two of the populations may not be resolved (separated) from each other and may overlap. As a result, all members of the one population cannot be reliably distinguished from the other populations in the data. Also, the one population and at least one other population may be characterized by overlapping ranges of signal values. Further aspects of cluster/population identification are presented below and in the references identified above under Cross-References, which are incorporated herein by reference.

Identification of partition populations may include assigning each partition to one of a plurality of predefined bins each corresponding to a distinct partition population or combination of partition populations. The predefined bins may represent all combinations of presence and absence (positivity and negativity) for the targets.

The reaction components and/or conditions of any of the multiplexed assays disclosed herein may be adjusted to achieve and/or improve resolution of different partition populations in the data. By changing the concentration of a particular assay within a multiplexed assay, the reaction efficiency for a particular target can be affected, which may result in a difference in signal level that allows populations detected with the same reporter and/or different reporters to be distinguished from one another. By changing reaction components/conditions, additional targets may be detected in the same multiplexed assay. In some cases, the signal amplitude for a target may be adjusted by varying the concentration of one or both primers for the target. Varying primer concentration without changing the reporter concentration may be useful in assays where the same reporter (e.g., a probe or a generic reporter) is used to detect two or more targets, but each of the two targets is amplified with at least one different primer. In some cases, the signal amplitude for a target may be adjusted by varying the concentration of a reporter for the target. In some cases, the signal amplitude for one or more targets may be adjusted by changing the annealing temperature used for thermocycling, the total concentration of dNTPs, the amounts of individual dNTPs relative to each other (e.g., if the targets have substantially different base compositions), or the like.

The data including all combinations of targets (i.e., all combinations of the presence or absence of each of the targets) will generally represent $2^R$ populations each having a different target content, where R is the number of different targets. For example, with three targets (A-C, R=3), there are eight populations: ( ) (A), (B), (C), (AB), (AC), (BC), and (ABC), each having a different target content. Some of the populations may overlap and/or may not be distinguishable from one another as well-resolved clusters. Some of the populations may overlap one another to form at least one heterogeneous cluster having a heterogeneous target content of one or more of the targets. Accordingly, less than $2^R$ well-resolved clusters may be produced as described elsewhere in the present disclosure.

Obtain Partition Counts.

A partition count for each partition population and/or cluster may be obtained. The partition count may be a value representing the number of partitions constituting a particular partition population or cluster. In some cases, the partition count may be obtained in part by summing two or more other partitions counts.

A number of partitions that are positive (or negative) for each target may be determined from the collected data. The signal(s) detected from each partition, and the partition itself, may be classified as being positive or negative for each of the targets contributing to the signal(s). Classification may be based on the amplitude (level) (and/or other suitable aspect) of the signal(s). For example, classification may be based on the intensity of light detected from the partition in a single optical channel or in two or more optical channels. If the signal(s)/partition is classified as being positive (+), for a given target, at least one copy of the target is deemed to be present in the partition. In contrast, if the signal(s)/partition is classified as negative (−), for a given target, the reaction corresponding to that target is deemed not to have occurred and no copy of the target is deemed to be present in the partition (i.e., the target is deemed to be absent from the partition).

Determination of Target Levels.

A level of the first target and the second target may be determined based on the collected data, indicated at 60. Each level may (or may not) be determined from only a subset of the collected data, such as, with selective exclusion of partitions positive for one or more other targets or for each other target. For example, the level of the first target may be determined based on a count of partitions positive only for the first target and a count of partitions negative for all targets. Similarly, the level of the second target may be determined based on a count of partitions positive only for the second target and a count of partitions negative for all targets.

A level of the third target may be determined, indicated at 62. The level determined may include an adjustment (interchangeably termed a correction) for overlapping populations of partitions. For example, the population of partitions positive for only the third target may overlap the population of partitions resulting from random co-localization of the first and second targets to the same partitions. The range of signal values for the populations may overlap in one channel or in each of a pair of channels. An estimated or predicted number of partitions in one or in each of the overlapping populations may be calculated, and a level of the third target determined based on the estimated or predicted number(s) (e.g., see Example 2).

Any suitable subset of the partitions may be excluded, for determining the level of a given target, without skewing the level determined, if the basis for exclusion is independent of the presence/absence of the target. For example, in an assay of targets A and B, all (or any suitable subset of) B-positive partitions may be excluded from determination of the level for target A, if being positive for B is independent of the presence or absence or A. (For example, there is no substantial association of targets A and B with each other when partitions are formed.) Accordingly, if all B-positive partitions are present in the same cluster (or two or more clusters), the entire cluster (or the two or more clusters) can be excluded from a determination of the level of target A, without skewing the result. As another example, in an assay for unlinked targets A, B, and C, the level of target A can be determined with all B-positives and all C-positives excluded, with only B-positives or only C-positives excluded, or with any combination of B-positives and C-positives excluded that is independent of the presence/absence of A (e.g., all BC-positives, whether A-negative or A-positive). In the same assay, the level of target B (or target C) may be determined from all of the data, if all B-positives (or all C-positives) are resolved from all other populations lacking a copy of target B (or target C). Alternatively, the level of target B (or target C) may be determined from only a subset of the data that excludes partitions independent of the presence/absence of B (or C).

Determination of target levels may (or may not) be based on each target having a Poisson distribution among the partitions. Each level may, for example, be a concentration value, such as a value representing the average number of copies of the target per partition or unit volume, among others. The partition data further or alternatively may be used (e.g., directly and/or as concentration data) to estimate copy number (CN) and copy number variation (CNV), or any other suitable property of the sample, using any suitable algorithms.

A level (e.g., concentration) of each target may be determined with Poisson statistics. The concentration may be expressed with respect to the partitions and/or with respect to a sample providing the target. The concentration of the target in the partitions may be calculated from the fraction of partitions that are positive for the target (or, equivalently, the fraction of partitions that are negative for the target) by assuming that copies of the target (before amplification) have a Poisson distribution among the partitions. With this assumption, the fraction f(k) of partitions having k copies of the target is given by the following equation:

$$f(k) = \frac{\lambda^k}{k!} e^{-\lambda} \qquad (1)$$

Here, $\lambda$ is the concentration of the target in the partitions, expressed as the average number of target copies per partition (before amplification). Simplified Poisson equations may be derived from the more general equation above and may be used to determine target concentration from the fraction of positive partitions. An exemplary Poisson equation that may be used is as follows:

$$\lambda = -\ln\left(1 - \frac{N_+}{N_{tot}}\right) \qquad (2)$$

where $N_+$ is the number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_+ + N_-)$) is equal to $f_+$, which is the fraction of partitions positive for the target (i.e., f+=f(1)+42)+43)+ . . . ) (see Equation 1), and which is a measured estimate of the probability of a partition having at least one copy of the target. Each number of partitions used to determine a level of a target has a value for the number.

Another exemplary Poisson equation that may be used is as follows:

$$\lambda = -\ln\left(\frac{N_-}{N_{tot}}\right) \qquad (3)$$

where $N_-$ and $N_{tot}$ are as defined above. $N_-/N_{tot}$ is equal to $f_0$, which is the fraction of negative partitions (or $1-f_+$), and is a measured estimate of the probability of a partition having no copies of the target, and $\lambda$ is the target concentration as described above.

Equations 2 and 3 above can be rearranged to produce the following equations:

$$\lambda = \ln(N_{tot}) - \ln(N_{tot} - N_+) \qquad (4)$$

$$\lambda = \ln(N_{tot}) - \ln(N_-) \qquad (5)$$

The concentration of each target in a multiplexed assay can, for example, be determined with any of Equations 2 to 5, using values (i.e., partition counts or calculated population values) obtained for $N_{tot}$ and $N_-$ or $N_+$, for each target. In some cases, the value used for $N_{tot}$ (the total partition count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the partition counts for all populations identified.

The value used for $N_-$ or $N_+$ is generally different for each target, and may result from summing the counts from a plurality of partition populations each containing a different combination of the targets being tested in the multiplexed assay. For example, with three targets (A, B, and C) in a multiplexed assay, the number of partitions positive for target A, $N_{+A}$, may be calculated as the sum of counts from the single (A only), double (AB and AC), and triple (ABC) positive populations, for use in Equation 2 or 4. Equivalently, the number of partitions negative for target A, $N_{-A}$, may be calculated, for use in Equation 3 or 5, as the difference between $N_{tot}$ and $N_{+A}$. Alternatively, the number of partitions negative for A may be calculated as the sum of counts from each population that is negative for target A, namely, in this example, a triple negative ("empty") population, two single positive populations (B and C), and one double positive population (BC). The same process may be repeated for each of the other targets using partition counts from the appropriate subset of populations.

In some embodiments, an estimate of the level of the target may be obtained directly from the positive fraction, without use of Poisson statistics. In particular, the positive fraction and the concentration (copies per partition) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because Poisson statistics takes into account the occurrence of multiple target copies per partition.

One of the targets in a multiplexed assay may be a reference (interchangeably termed a reference target or reference sequence). The reference may provide a standard against which one or more of the other targets can be compared. For example, the reference may be an endogenous or internal reference provided by the sample itself or an exogenous or external reference added to the sample during sample preparation. In exemplary embodiments, the reference and the other targets being assayed are provided by the same sample of nucleic acid, such as obtained from the same subject and provided by copies of the same genome. The reference may have a known copy number in the genome. Accordingly, the copy number of one or more of the other targets can be determined by comparing the level of the other target(s) with the reference. As an example, if the reference (a first target) has a copy number of 1 in the source genome and a concentration of 1.0 copy per partition in the assay, and a second target has a concentration of 0.5 copy per partition in the assay, then the second target has a copy number of 0.5. The copy number may provide an indication of the frequency at which the second target is deleted in the sample. For example, hemizygous deletions of cancer-related genes may promote cancer and are detectable by a copy number variation/difference relative to a normal sample and/or relative to the copy number of the reference. Diploid cells contain two haploid genomes per cell. Therefore, a sample containing diploid cells, and/or nucleic acid prepared therefrom, may have a copy number of 0.5 for a target that exhibits a hemizygous deletion in each of the diploid cells.

At least a pair of targets in the sample may represent different forms of a gene of interest, such as a variant form (also called a mutant form) and a normal form (also called a wild-type form). The different forms may be alternate forms of the gene of interest that differ in sequence at one or more nucleotide positions, such as differing by a single nucleotide, or two, three, or more nucleotides, and/or differing by an insertion, duplication, or deletion, among others. The variant form may be a comparatively rare form of the gene and the normal form may be a comparatively abundant form of the gene for a species of organism (and/or a type of cell) represented by the sample. For example, the variant form may be predominant in fewer than about 10%, 5%, or 1%, among others, of members of a population of interest from the species of organism or cells of the type of cell. Also or alternatively, the normal form may be predominant in greater than about 10%, 25%, or 50% (a majority) of members of the population of interest from the species of organism or cells of the type of cell.

The at least a pair of targets may include a target that is a variant sequence (from a variant form of the gene of interest) and an other target that is a normal sequence (from a normal form of the gene of interest). The variant sequence and the normal sequence may overlap each other in the gene of interest to define a region of overlap. The variant sequence and the normal sequence may differ from each other by at least one nucleotide in the region of overlap. In some cases, the region of overlap may differ by at least, or no more than 1, 2, or 3 nucleotides between the variant sequence and the normal sequence. The region of overlap may be at least 1, 2, 5, or 10 nucleotides, among others. In some examples, the region of overlap may be the same length as the variant sequence and/or the normal sequence.

The gene of interest may be a cancer-related gene. Exemplary cancer-related genes that may be suitable include proto-oncogenes (e.g., Akt-1, Akt-2, Fos, Jun, Myc (C-Myc, L-Myc, N-Myc), Ras (H-Ras, K-Ras, N-Ras), Rel, Wnt-1, Erb-B2, Myb, B-Raf, CTNNB1, etc.), tumor suppressor genes (e.g., TGF-β, NF-1, NF-2, APC, PTEN, SMAD-2, SMAD-4, Rb, p53, WT-1, p16, BRCA-1, BRCA-2, KLF6, etc.), metastasis genes (e.g., Mtdh, Cadm1, etc.), and the like.

Figure 2:
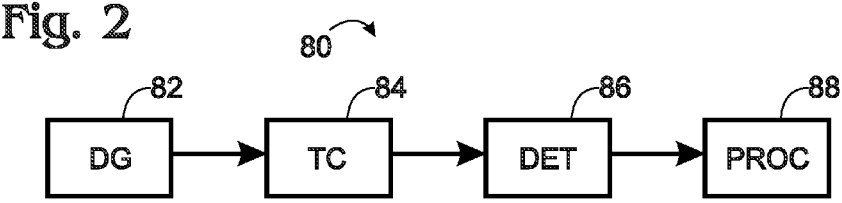
FIG. 2 is a schematic view of an exemplary system for performing the multiplexed digital assay of FIG. 1, in accordance with aspects of the present disclosure.

FIG. 2 shows an exemplary system 80 for performing the digital assay of FIG. 1. System 80 may include a partitioning assembly, such as a droplet generator 82 ("DG"), a thermal incubation assembly, such as a thermocycler 84 ("TC"), a detection assembly (a detector) 86 ("DET"), and a data processing assembly (a data processor) 88 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets), or signals/data, between the assemblies. Any suitable combination of the assemblies may be operatively connected to one another, and/or one or more of the assemblies may be unconnected to the other assemblies, such that, for example, material/data are transferred manually.

Detector 86 may provide a plurality of optical channels in which data can be collected. The detector may or may not have a distinct sensor or detection unit for each optical channel.

System 80 may operate as follows. Droplet generator 82 may form droplets disposed in a continuous phase. The droplets may be cycled thermally with thermocycler 84 to promote amplification of targets in the droplets. Signals may be detected from the droplets with detector 86. The signals may be processed by processor 88 to determine droplet counts and/or target levels, among others. The system may include a program, optionally residing on a computer-readable storage medium, and comprising instructions for causing the data processor and/or controller to perform and/or control any suitable combination of the steps disclosed herein, such as in FIG. 1.

Further aspects of sample preparation, partition formation (such as droplet generation), data collection, population identification and/or cluster assignment, obtaining partition counts, and target level determination, among others, that may be suitable for the system of the present disclosure are described elsewhere in the present disclosure, and in the references identified above under Cross-References, which are incorporated herein by reference.

II. EXAMPLES

This section presents selected aspects and embodiments of the present disclosure related to methods of performing multiplexed digital assays with unresolved populations of partitions that are positive for different target combinations (of one or more targets).

Example 1

Assay Configurations

This example describes exemplary assay configurations for target amplification and detection of amplification with reporters; see FIGS. 3-7.

Figure 3:
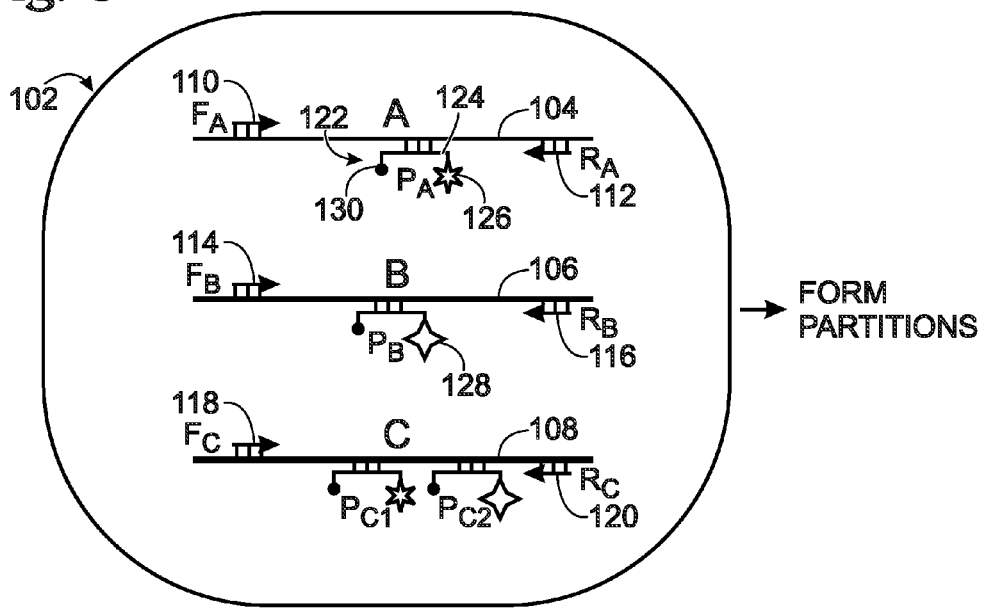
FIG. 3 is a schematic diagram illustrating an exemplary multiplexed digital assay performed in partitions on at least three targets (targets A, B, and C), with the strategy for target amplification in partitions and detection with specific probes presented in an exemplary bulk phase, in accordance with aspects of the present disclosure.

FIG. 3 shows a schematic diagram illustrating selected aspects of an exemplary multiplexed digital assay that may be performed according to FIG. 1. The assay may be performed with at least one bulk phase 102 divided into fluid volumes that directly (or in combination with other fluid volumes from one or more other bulk phases) form partitions, such as droplets. Bulk phase 102 contains copies of three templates 104, 106, and 108 (e.g., nucleic acid templates, such as DNA, RNA, or a combination thereof, among others), each of which will be present at partial occupancy in the partitions when the partitions are formed. Each template, shown schematically here, may be double-stranded or single-stranded. Copies of each template may be uniform or variable in length. The templates may be unrelated or related in sequence. For example, here, templates 104-108 contain unrelated sequences, which are indicated schematically by different line weights for the three templates.

Each template (104, 106, and 108) provides a target region (a target or target sequence) for amplification. Template 104 contains target A, which is amplifiable with a pair of primers 110, 112, namely, a forward primer, $F_A$, and a reverse primer, $R_A$, to generate copies of an amplified target (interchangeably termed an amplicon). Template 106 contains target B, which is amplifiable with a different pair of primers 114, 116, namely, a forward primer, $F_B$, and a reverse primer, $R_B$. Finally, template 108 contains target C, which is amplifiable with yet another pair of primers 118, 120, namely, a forward primer $F_C$, and a reverse primer, Rc. Specific binding of each primer to the corresponding template (and/or amplified target/amplicon) is determined by via base pairs, which are shown schematically as a trio of vertical bars extending from the template to each primer. (The actual number of base pairs is not shown.) Each primer may be capable of base pairing with the template along the entire length of the primer, may be a 5'-tailed primer that does not base pair with the template at the 5' end of the tailed primer, and/or may be a mismatched primer that has one or more mismatches with the template when base paired with the template, among others.

Amplification of each target may (or may not) be detectable with a distinct reporter 122, such as a target-specific probe (e.g., a Taqman® probe as shown here). Amplification of the targets may be reported with respective target-specific probes, namely $P_A$ for target A, $P_B$ for target B, and a single probe or at least a pair of probes, $P_{C1}$ and $P_{C2}$, for target C. Each probe may bind specifically to the target and/or amplicon. The probe may include an oligonucleotide 124, and at least one luminophore (e.g., a fluorophore, such as fluorophore 126 or 128) and a quencher 130 attached to the oligonucleotide. The oligonucleotide may provide target specificity by hybridization predominantly or at least substantially exclusively to only one target. Each of the fluorophore and the quencher may (or may not) be conjugated to the oligonucleotide by a covalent bond. The probe also or alternatively may include a binding moiety (a minor groove binder) for the minor groove of a DNA duplex, which may be conjugated to the oligonucleotide and which may function to permit a shorter oligonucleotide to be used in the probe. In any event, amplification may modify the reporter, such as by degradation of oligonucleotide 124, to separate fluorophore 126 from quencher 130. The fluorophore then is capable of fluorescing more brightly when irradiated with excitation light, because the effect of the quencher on light emission is reduced or eliminated. Quencher 130 is configured to quench light emission from the fluorophore in a proximity-dependent fashion. Accordingly, light detected from the fluorophore may increase when the associated oligonucleotide binds to the amplified target, to increase the separation between the fluorophore and the quencher, or when the probe is cleaved and the fluorophore and quencher become uncoupled during target amplification, among others. The quencher may be the same or different for each fluorophore. Here, the assay is designed so that the presence of a target leads to an increase in corresponding intensity, because amplification reduces quenching. In other assays, the reverse could be true, such that the presence of a target caused a decrease in corresponding intensity (although it typically is easier to detect a signal against a dark background than the opposite). Moreover, some embodiments may be constructed without a quencher, so long as the fluorescence and so the signal changes upon amplification.

The target-specific probes, $P_A$, $P_B$, and $P_{C1}$ plus $P_{C2}$) may be spectrally distinct due to distinct fluorophores. $P_A$ includes fluorophore 126, $P_B$ includes different fluorophore 128, and the pair of target C probes collectively includes both fluorophores 126 and 128.

The fluorophores attached to the respective oligonucleotides of the probes may be the same or different. The fluorophores may produce signals in different channels or detectable but distinguishable signals in the same channel, allowing multiplexing in that channel. The signals may be distinguishable because an aspect of the fluorescence is different for one fluorophore relative to the other fluorophore(s). For example, the intensity associated with one fluorophore, following reaction, may be lower or higher than the intensity(ies) associated with the other fluorophore(s). In some embodiments, one probe may be labeled with a different number of fluorophores than the other probe, and/or the probes may be located in slightly different local environments, creating a different level of fluorescence for each probe following reaction. Alternatively, or in addition, both probes may be labeled with the same number of fluorophores (e.g., one fluorophore), but there may be more or less of one probe than the other in the sample, so that a greater or smaller signal is created when the reactions have occurred. In some cases, the fluorophores themselves might be different, with one more or less intrinsically fluorescent than the other (e.g., due to differences in extinction coefficient, quantum yield, etc.). Exemplary fluorophores that may be suitable include FAM, VIC, HEX, ROX, TAMRA, JOE, etc., among others. In some cases, different concentration of primers for two or more of the targets may produce different amounts of amplification, which in turn may result in distinguishable amplification signals.

The targets may be substantially unlinked when the partitions are formed, such as having a degree of linkage of less than about 10%, 5%, or 1%, among others. Targets that are not substantially linked can co-localize to the same partitions by chance in direct relation to the concentrations of the targets. The targets may be unlinked from one another naturally (e.g., being present on different chromosome) or a linkage of the targets to one another may be eliminated by sample processing, such as nuclease digestion (e.g., with a restriction enzyme), shearing, or the like.

Figure 4:
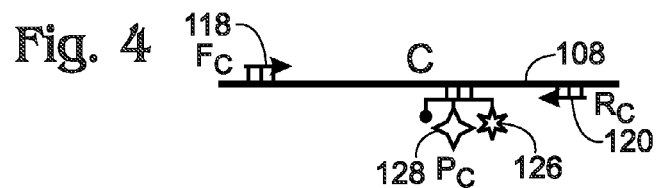
FIG. 4 is a schematic view of another strategy for detection of target C amplification in the multiplexed digital assay of FIG. 3, by use of a double-labeled probe, in accordance with aspects of the present disclosure.

FIG. 4 schematically illustrates another strategy for detection of target C amplification in the multiplexed digital assay of FIG. 3. Rather than a pair of C-specific probes, as in FIG. 3, a single double-labeled probe, $P_C$, may be utilized for target C. The probe may be labeled with the same fluorophores 126 and 128 as probes $P_A$ and $P_B$ collectively.

Figure 5:
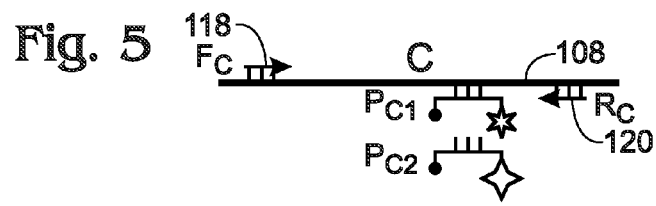
FIG. 5 is a schematic view of still another strategy for detection of target C amplification in the multiplexed digital assay of FIG. 3, by use of a pair of spectrally distinct probes that bind to the same region of the target, in accordance with aspects of the present disclosure.

FIG. 5 schematically illustrates another strategy for detection of target C amplification in the multiplexed digital assay of FIG. 3. The assay may include at least a pair of different probes, $P_{C1}$ and $P_{C2}$, that bind the same region of target C (or amplicons produced therefrom). Each member of the pair may be labeled with a different luminophore, such as fluorophore 126 for probe $P_{C1}$ and fluorophore 128 for probe $P_{C2}$. The probes may or may not include the same nucleic acid or nucleic acid sequence.

Figure 6:
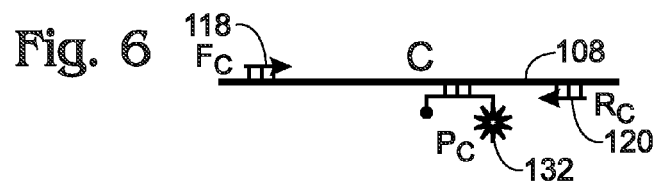
FIG. 6 is a schematic view of yet still another strategy for detection of target C amplification in the multiplexed digital assay of FIG. 3, by use of a probe labeled with a different fluorophore than the probes for targets A and B, in accordance with aspects of the present disclosure.

FIG. 6 schematically illustrates another strategy for detection of target C amplification in the multiplexed digital assay of FIG. 3. The assay may include a single probe, $P_C$, for target C that is labeled with a different luminophore, fluorophore 132, than fluorophores 126, 128 of probes $P_A$ and $P_B$. Fluorophore 132 may be spectrally distinct from fluorophores 126, 128 and may be detectable in the same channels (e.g., light emission is detected in the same wavelength ranges) as fluorophores 126, 128, respectively.

In some embodiments, amplification of at least one of the targets may be detected with a generic reporter, such as an intercalating dye. For example, the same generic reporter may report amplification of all three targets or any subset thereof. In some cases, a generic reporter may be used in combination with one or more target-specific probes to detect amplification of the targets.

Figure 7:
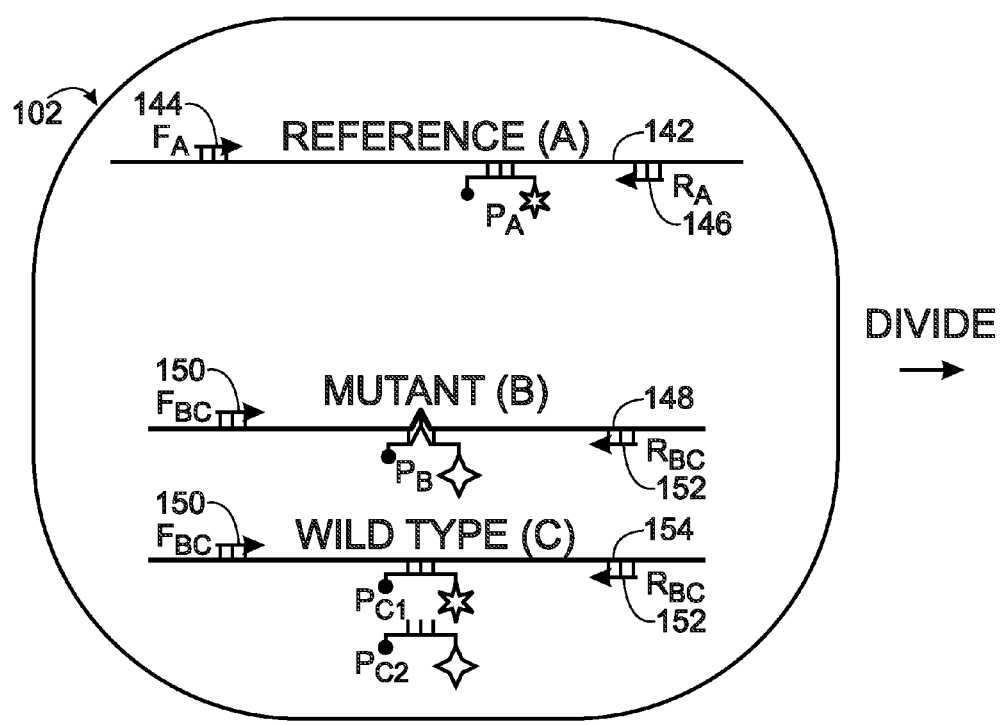
FIG. 7 is a schematic diagram illustrating an exemplary multiplexed digital assay performed generally as in FIGS. 3 and 5, where target A is a reference sequence having a known copy number, target B is a variant sequence from a gene of interest, and target C is a normal sequence from the gene of interest, in accordance with aspects of the present disclosure.

FIG. 7 is a schematic diagram illustrating an exemplary multiplexed digital assay performed generally as in FIGS. 3 and 5. Target A is a reference amplified from copies of template 142 with a pair of primers 144, 146. Target A has an expected (e.g., known) or assumed copy number, such as a copy number of 1 or 2, among others, per genome (such as per diploid genome, haploid genome, or the like). Target B represents a variant form of a gene of interest and is amplified from copies of template 148 with a pair of primers 150, 152. Target C represents a normal form of the gene of interest and is amplified from copies of template 154 with the same pair of primers 150, 152 as target B. Amplification of targets B and C may be distinguished with target-specific probes. Target B is detected with a probe, $P_B$, that binds selectively to the variant target relative to the normal target (and/or amplicons therefrom). Similarly, target C is detected with a pair of probes, $P_{C1}$ and $P_{C2}$, that each bind selectively to the same region of the normal target and selectively relative to the variant target (and/or amplicons therefrom). The pair of probes may bind to the same strand of the target/amplicon or to distinct strands thereof. In other cases, only a single probe may be utilized to detect amplification of target C, such as any of the single probes of FIGS. 4 and 6, among others. In other embodiments, one or more the probes for target B or C may be a labeled primer for selective amplification of the target.

Example 2

Data Collection and Processing

This example describes exemplary collected data and exemplary approaches for processing the collected data; see FIGS. 8-15.

FIG. 8 shows a pair of fragmentary graphs illustrating a portion of exemplary fluorescence intensity data that may be collected from partitions formed according to any of FIGS. 3-7 after target amplification in the partitions. The data may be detected in a single channel (a single wavelength regime) or in a pair of channels (a pair of distinct wavelength regimes), among others. The data may be collected serially, such as with the partitions moving through a detection region, as shown here, or in parallel, such as by imaging, among others. In any event, the data may provide one or more signal values for each partition (or signal event), such as a signal amplitude for the partition in only one channel or in at least a pair of channels.

Each of the partitions may be classified as positive or negative for each target based on the signal amplitude(s) for the partition. For example, the signal amplitude(s) may be compared to one or more thresholds or ranges to classify the partition.

Exemplary aligned pairs of signal peaks for various types of positives are labeled on the graph: triple negative(−), positive for A only (A), positive for B only (B), positive for C only or only A and B (C|AB), positive for only A and C (AC), positive for only B and C (BC), and positive for all three targets (ABC). At least two distinct types of target-positive partitions may be difficult to reliably distinguish. For example, here, a partition that is positive only for target C cannot be reliably distinguished from a partition that is positive for only targets A and B.

FIG. 9 shows a schematic view of a scatter plot of the fluorescence data of FIG. 8. Each partition (or "event") is graphed as a data point. Here, the assay is configured according to any of FIGS. 3, 4, 5, and/or 7, with channel 1 detecting emission from fluorophore 126 (targets A and C) and channel 2 detecting emission from fluorophore 128 (targets B and C). The data point for each partition is positioned in the plot according to fluorescence amplitude detected in each channel for the partition. Individual data points are not shown. Instead, each cluster or population of partitions/data points is represented schematically by a circle, although the relative numbers of data points in the various populations are not indicated. The population of partitions that are only C-positive (C) are unresolved (not separated) from the population of partitions that are positive only for targets A and B (AB). However, the A-only (A), B-only (B), and triple-negative populations (−) are distinguishable.

The AB population interchangeably may be termed a first population or an alpha population, and the C-only population interchangeably may be termed a second population or a beta population. The alpha population may not be separated from the beta population in a plot of the collected data. In other words, the alpha population may define an area in plot that at least partially overlaps an area defined by the beta population, and vice versa. Stated differently, the alpha population may have a detected signature in the data that overlaps a detected signature for the beta population. The signature may be defined by signals detected from partitions in any suitable number of different optical channels, such as one, two, three, or more. The signals detected in each optical channel for the alpha population may have a range of values that at least partially overlaps a range of values of signals detected for the beta population in the same channel. Accordingly, the plot may have a different channel represented by each axis of the plot. In other cases, the plot may have an axis that represents time or event (partition) number, among others, and one or more axes representing one or more different channels.

FIGS. 10 and 11 show the scatter plot of FIG. 9 modified to illustrate an exemplary approach for calculating the concentration of each of targets A and B from only a subset of the collected data. In FIG. 10, partitions positive for target B (alone or in combination with one or more other targets) and partitions positive for target C (alone or in combination with one or more other targets) are excluded from the calculation. Accordingly, the concentration of target A, $\lambda_A$, can be calculated based on Equation 5 above as follows:

$$\lambda_A = \ln(N_A + N_0) - \ln(N_0) \qquad (6)$$

where $N_A$ is the count of A-only positives and $N_0$ is the count of completely negative partitions. In FIG. 11, partitions positive for target A (alone or in combination with one or more other targets) and partitions positive for target C (alone or in combination with one or more other targets) are excluded from the calculation. Accordingly, the concentration of target B can be calculated based on Equation 5 above as follows:

$$\lambda_B = \ln(N_B + N_0) - \ln(N_0) \qquad (7)$$

where $N_B$ is the count of B-only positives and $N_0$ is the count of completely negative partitions.

FIG. 12 shows the scatter plot of FIG. 9 in a modified form to illustrate an exemplary approach for calculating the concentration of target C from only a subset of the collected data. The concentration can be calculated with an adjustment (interchangeably termed a correction) for overlapping population AB. In other words, an estimate of the abundance of partitions in population AB can be calculated and subtracted from the count for the overlapping populations (C|AB). In FIG. 12, partitions positive for target A (alone or in combination with one or more other targets) and partitions positive for target B (alone or in combination with one or more other targets) are excluded from the calculation. Accordingly, the concentration of target C can be calculated based on Equation 5 above as follows:

$$\lambda_C = \ln(N_C + N_0) - \ln(N_0) \qquad (8)$$

where $N_C$ is the number of C-only positives, $N_0$ is the count of completely negative partitions. However, since $N_C$ cannot be counted because of overlap with the AB-positive population, the number of C-only positives can be calculated as follows:

$$N_{C\text{-}calc} = N_{C|AB} - \left(\frac{N_A N_B}{N_0}\right) \qquad (9)$$

where $N_{C|AB}$ is the count of the overlapped populations of C-only and AB-only positives, and the last term in parentheses is a calculated number of the AB positives expected by chance. Accordingly, the calculated number of C-only positives, $N_{C\text{-}calc}$, can be used in Equation 8 to provide an adjusted/corrected $N_{tot}$ for calculation of the concentration of target C.

FIG. 13 shows the scatter plot of FIG. 9 in a modified form to illustrate another exemplary approach for calculating the concentration of target C, in this case with all of the plotted data represented. The concentration of target C can be calculated based on Equation 5 above as follows:

$$\lambda_C = \ln(N_{tot}) - \ln(N_{Cneg}) \qquad (10)$$

where $N_{tot}$ is the total partition count, irrespective of target content, and $N_{Cneg}$ is the number of C-negative partitions, which can be calculated as follows:

$$N_{Cneg} = N_0 + N_A + N_B + \frac{N_A N_B}{N_0} \qquad (11)$$

where the last term in Equation 11 is an expected number of AB positives resulting from co-localization of targets A and B in the same partitions by chance.

Equations 6, 7, and 10 above provide approaches for estimating the concentrations of targets A, B and C, respectively. A shortcoming of these equations is they rely on a subset of the total available data, namely, a fraction of the total number of partitions. It is often true that increasing the number of partitions analyzed will result in an improvement in the accuracy of the measurement. Other strategies for estimating concentrations of the targets using larger subsets of the partitions are presented below.

Equation 6 above provides for estimation of the concentration of target A. However, the data ($N_A$, $N_0$) may be susceptible to sampling error which can affect the concentration estimate:

$$\Delta \lambda_A = \frac{1}{(N_A + N_0)} \Delta N_A + \frac{1}{(N_A + N_0)} \Delta N_0 - \frac{1}{(N_0)} \Delta N_0$$
$$= \frac{N_A}{(N_A + N_0)} \left[ \frac{\Delta N_A}{N_A} - \frac{\Delta N_0}{N_0} \right]$$

Assuming that the errors in $N_A$ and $N_0$ are uncorrelated, the magnitude of the concentration error is:

$$|\Delta \lambda_A|^2 = \left[ \frac{N_A}{(N_A + N_0)} \right]^2 \left[ \left( \frac{\Delta N_A}{N_A} \right)^2 + \left( \frac{\Delta N_0}{N_0} \right)^2 \right]$$

Further assuming that the sampling errors are proportional to the square root of the number of each partition species:

$$|\Delta \lambda_A|^2 = \left[ \frac{N_A}{N_A + N_0} \right]^2 \left[ \frac{1}{N_A} + \frac{1}{N_0} \right]$$

With reference to FIG. 10, the concentration of A could also be determined from the numbers of partitions in the BC and ABC clusters:

$$\lambda_A = \ln(N_{ABC} + N_{BC}) - \ln(N_{BC})$$

In this case the error is estimated as:

$$|\Delta \lambda_A|^2 = \left[ \frac{N_{ABC}}{N_{ABC} + N_{BC}} \right]^2 \left[ \frac{1}{N_{ABC}} + \frac{1}{N_{BC}} \right]$$

The two equations above are expected to give similar, though not necessarily identical, estimates of the concentration of A. The error of each estimate could be calculated, and the method of estimation could be chosen based on which has the lower error. This will typically be the subset with the greatest number of events: the error for the first equation decreases with increasing $N_A$ and $N_0$, and the error for the second decreases with increasing $N_{ABC}$ and $N_{BC}$.

To further improve the estimate of the concentration of A these data could be combined. Then:

$$\lambda_A = \ln[(N_A + N_0) + (N_{ABC} + N_{BC})] - \ln(N_0 + N_{BC})$$

For this equation the estimate of the error is:

$$\Delta \lambda_A = \frac{1}{[(N_A + N_0) + (N_{ABC} + N_{BC})]} [\Delta N_A + \Delta N_0 + \Delta N_{ABC} + \Delta N_{BC}] -$$
$$\frac{1}{[N_0 + N_{BC}]} [\Delta N_0 + \Delta N_{BC}]$$

$$\Delta \lambda_A = \frac{N_A}{[(N_A + N_0) + (N_{ABC} + N_{BC})]} \frac{\Delta N_A}{N_A} +$$

-continued $$\frac{N_{ABC}}{[(N_A + N_0) + (N_{ABC} + N_{BC})]} \frac{\Delta N_{ABC}}{N_{ABC}} -$$

$$\left\{ \frac{[N_A + N_{ABC}]}{[(N_A + N_0) + (N_{ABC} + N_{BC})]} \frac{N_0}{[N_0 + N_{BC}]} \right\} \frac{\Delta N_0}{N_0} -$$

$$\left\{ \frac{[N_A + N_{ABC}]}{[(N_A + N_0) + (N_{ABC} + N_{BC})]} \frac{N_{BC}}{[N_0 + N_{BC}]} \right\} \frac{\Delta N_{BC}}{N_{BC}}$$

Again assuming the errors are uncorrelated and that they decrease with the square root of partition count:

$$|\Delta \lambda_A|^2 = \left[ \frac{N_A}{(N_A + N_0) + (N_{ABC} + N_{BC})} \right]^2 \frac{1}{N_A} +$$

$$\left[ \frac{N_{ABC}}{(N_A + N_0) + (N_{ABC} + N_{BC})} \right]^2 \frac{1}{N_{ABC}} +$$

$$\left[ \frac{N_A + N_{ABC}}{(N_A + N_0) + (N_{ABC} + N_{BC})} \right]^2 \left[ \frac{N_0}{N_0 + N_{BC}} \right]^2 \frac{1}{N_0} +$$

$$\left[ \frac{N_A + N_{ABC}}{(N_A + N_0) + (N_{ABC} + N_{BC})} \right]^2 \left[ \frac{N_{BC}}{N_0 + N_{BC}} \right]^2 \frac{1}{N_{BC}}$$

By making estimates of the amount of overlap between the AB and C clusters as in Equation 11, it is possible to estimate the concentration of A using essentially all of the partition information:

$$\lambda_A = \ln [(N_A + N_0) + (N_{AB} + N_B) + (N_{AG} + N_C) + (N_{ABC} + N_{BC})] - \ln(N_0 + N_B + N_C + N_{BC})$$

The first bracketed term is the total number of partitions. In the second bracketed term, all of the quantities except $N_C$ are observed directly. $N_C$ can be estimated from Equation 9:

$$N_{C\text{-}calc} = N_{C|AB} - \frac{N_A N_B}{N_0}$$

Or from a similar equation:

$$N_{C\text{-}calc} = N_{C|AB} - \frac{N_{AC} N_{BC}}{N_{ABC}}$$

FIG. 14 shows another exemplary schematic view of a scatter plot that may result from the fluorescence data of FIG. 8. FIG. 14 differs from FIG. 9 in that populations AC, BC, and ABC overlap one another. However, the approach described for FIGS. 10-12 or FIGS. 10, 11, and 13 still may be implemented to determine target levels and/or one or more copy numbers of one or more targets.

FIG. 15 shows still another exemplary schematic view of a scatter plot that may result from the fluorescence data of FIG. 8. FIG. 15 differs from FIG. 9 in that the C-only population does not overlap the AB-only population. Accordingly, the concentration of each target may be calculated by ignoring the double-positive and triple-positive populations, using Equations (6) and (7) for targets A and B, and the following equation for target C:

$$\lambda_C = \ln(N_C + N_0) - \ln(N_0) \quad (12)$$

Example 3

Selected Embodiments I

This example describes selected embodiments of the present disclosure.

Existing Taqman® mutation assays (e.g., K-RAS, B-RAF, etc.) could be used, for example, along with existing CNV reference assays. Testing and validation may require samples with known mutations and/or hemizygous deletions.

In an exemplary multiplexed K-RAS assay, the same primers may be used to amplify wild-type and mutant K-RAS targets. One probe in the assay may target a wild-type K-RAS target sequence, and one or more other probes in the assay may target a mutation (e.g., a single base mutation) of the target sequence. In addition, the multiplexed assay may have a reference sequence, such as from an RPP 30 gene, as a reference target.

Hemizygous deletions (i.e., the copy number of the target sequence is 0.5 rather than a normal 1) may also be a frequent phenomenon in cancers, in addition to single-base mutations. The present disclosure describes a multiplexed digital assay that can detect the occurrence of a hemizygous deletion and a single-base mutation in a target gene.

The idea is to do copy number analysis (i.e., CNV) using the wild-type signal of a single base (e.g., SNP) mutation assay. This should allow for detection of mutations (via reference to the wild-type probe), as well as ascertainment of the target CNV status (e.g., hemizygous) using the same wild type probe (and a reference target assay).

In the cases when the target is expected to have no linkage to the reference, a scheme where only two colors are used can be employed for a single-well experiment. An embodiment is as follows: label reference in HEX dye, label mutant in FAM dye, label wild type in FAM dye and HEX dye (e.g., equimolar). The concentration of reference then may be computed from the FAM-negative droplets only, the concentration of the mutant may be determined from the HEX-negatives only, the concentration of the wild type may be determined from the double positives after a correction for the expected double positives due to incorporation of mutant and reference in the same droplet. (These are expected to be a small number due to the typically low concentration of a mutant). The two dyes described need not be FAM dye or HEX dye; those are used for illustration purposes.

Two pieces of useful diagnostic information can be obtained from one multiplexed assay. A single multiplexed assay could simultaneously address mutation(s) and hemizygous deletions. Currently, such information is obtained via two (or more) separate assays. The use of a single well adds robustness and self-normalization of the results.

Example 4

Selected Embodiments II

This example described selected embodiments of the present disclosure, presented as a series of numbered paragraphs.

1. A method of performing a multiplexed digital assay, the method comprising: (A) providing partitions containing a first target, a second target, and a third target each at partial occupancy, wherein a plurality of the partitions each contain a copy of the first target and the second target; (B) collecting data representing signals from one or more reporters for each target in the partitions, wherein a first population of partitions positive for the first and second targets is not resolved in the data from a second population of partitions positive for only the third target; (C) determining a level of the first target and the second target from the data; (D) calculating a number of partitions in the first population, the second population, or each of the first and second populations based on the data; and (E) determining a level of the third target based in part on the number of partitions calculated.

2. The method of paragraph 1, wherein the step of determining a level of the first target is performed with data for only a subset of the partitions that selectively excludes partitions positive for the second target and partitions positive for the third target, and wherein the step of determining a level of the second target is performed with data for only a subset of the partitions that selectively excludes partitions positive for the first target and partitions positive for the third target.

3. The method of paragraph 1 or 2, wherein the step of calculating a number of partitions is based on a count of partitions positive for only the first target, a count of partitions positive for only the second target, and a count of partitions negative for all three targets.

4. The method of any of paragraphs 1 to 3, further comprising a step of amplifying the targets in the partitions.

5. The method of any of paragraphs 1 to 4, wherein one of the targets is a reference having an expected or assumed copy number, and wherein another of the targets represents a normal form of a gene of interest, further comprising a step of determining a copy number of the normal form of the gene of interest by comparing the level of the normal form to the level of the reference.

6. The method of paragraph 5, wherein yet another of the targets represents a mutant form of the gene of interest.

7. The method of paragraph 6, wherein the first target is the reference and the second target represents the mutant form.

8. The method of any of paragraphs 1 to 7, wherein the first target and the second target are substantially unlinked to each other when the partitions are formed.

9. The method of any of paragraphs 1 to 8, wherein the second target and the third target each represent a cancer-related gene.

10. A method of performing a multiplexed digital assay, the method comprising: (A) providing partitions containing a first target as a reference, a second target representing a variant form of a cancer-related gene, and third target representing a normal form of the cancer-related gene, each target being present at partial occupancy; (B) collecting data for amplification of the targets in the partitions; (C) determining a copy number of the third target from the data by comparing a level of the third target to a level of the first target; and (D) determining a level of the second target based on the data.

Example 5

Selected Embodiments III

This example described selected embodiments of the present disclosure, presented as a series of numbered paragraphs.

1. A method of performing a multiplexed digital assay, the method comprising: (A) forming partitions each including a portion of a same sample, the sample including a first target that is a reference sequence, a second target that is a variant sequence from a gene of interest, and a third target that is a normal sequence from the gene of interest; (B) amplifying the first target, the second target, and the third target in the partitions; (C) collecting data from a plurality of the partitions for amplification of each of the targets; (D) determining a level of the second target; and (E) determining a copy number of the third target from a level of the first target and a level of the third target.

2. The method of paragraph 1, wherein the gene of interest is a cancer-related gene.

3. The method of paragraph 1 or paragraph 2, wherein the variant sequence and the normal sequence overlap each other in the gene of interest to define a region of overlap, and wherein the variant sequence and the normal sequence differ by at least one nucleotide in the region of overlap.

4. The method of any of paragraphs 1 to 3, wherein, in the data collected, signals for an alpha population of partitions positive for each of the first and second targets have a range that overlaps corresponding signals for a beta population of partitions positive for only the third target.

5. The method of paragraph 4, further comprising a step of determining a level of the first target, wherein the steps of determining a level of the first target and determining a level of the second target are each performed with only a portion of the data that excludes the alpha population and the beta population.

6. The method of paragraph 5, wherein the step of determining a level of the first target is performed with values obtained from only a portion of the data that selectively excludes partitions positive for the second target and partitions positive for the third target, and wherein the step of determining a level of the second target is performed with values obtained from only a portion of the data that selectively excludes partitions positive for the first target and partitions positive for the third target.

7. The method of paragraph 5, further comprising a step of determining a level of the third target based at least in part on a value for a number of partitions in the alpha population.

8. The method of paragraph 7, wherein the step of determining a level of the third target includes a step of calculating a level of the third target with a value for a total number of partitions including partitions in the alpha population, partitions in the beta population, partitions in a population positive only for the first target, and partitions in a population positive only for the second target.

9. The method of paragraph 8, wherein the step of calculating a level of the third target is performed with the value for a total number of partitions and a value for a number of partitions in the beta population or a value for a number of partitions negative for the third target.

10. The method of any of paragraphs 1 to 9, wherein the data are collected in no more than two different optical channels.

11. The method of any of paragraphs 1 to 10, wherein the sample includes copies of at least one genome that provides the targets, and wherein the reference has a known copy number in the at least one genome.

12. The method of any of paragraphs 1 to 11, further comprising a step of determining a copy number of the second target from the level of the first target and the level of the second target.

13. The method of paragraph 1, wherein each partition contains a plurality of different probes collectively sensitive to amplification of any one of the targets and each specifically sensitive to amplification of only one of the targets.

14. The method of any of paragraphs 1 to 13, wherein each partition includes a generic reporter that is sensitive to amplification of each of the targets.

15. The method of any of paragraphs 1 to 14, wherein the partitions include a first probe sensitive to amplification of the first target and labeled with a first luminophore, a second probe sensitive to amplification of the second target and labeled with a second luminophore different from the first luminophore, and a third probe sensitive to amplification of the third target and labeled with the first luminophore and the second luminophore.

16. The method of paragraph 15, wherein the third probe includes a probe labeled with the first luminophore and not the second luminophore and another probe labeled with the second luminophore and not the first luminophore.

17. The method of any of paragraphs 1 to 16, wherein the data are collected from the plurality of partitions at about a same temperature.

18. The method of any of paragraphs 1 to 17, wherein the step of collecting data is performed after the step of amplifying has been completed.

19. The method of any of paragraphs 1 to 18, wherein the first target and the second target are not substantially linked to each other when the partitions are formed.

20. A method of performing a multiplexed digital assay, the method comprising: (A) forming partitions each including a portion of a same fluid volume that contains a first target, a second target, and a third target; (B) amplifying the first target, the second target, and the third target in the partitions; (C) collecting data from a plurality of the partitions for amplification of each of the targets, wherein in the data an alpha population of partitions each positive for both of the first and second targets at least partially overlaps a beta population of partitions positive for only the third target; (D) determining a level of the first target and a level of the second target from only a portion of the data that excludes both the alpha population and the beta population; (E) determining a number of partitions in the alpha population; and (F) determining a level of the third target based in part on the number of partitions in the alpha population.

21. The method of paragraph 20, wherein the step of determining a level of the third target includes a step of calculating a number of partitions in the beta population based at least in part on the number of partitions in the alpha population.

22. The method of paragraph 21, wherein the step of calculating a number of partitions in the beta population includes a step of subtracting the number of partitions in the alpha population from a number of partitions in both populations combined.

23. The method of any of paragraphs 20 to 22, wherein the step of determining a level of the third target includes a step of determining a combined number of partitions negative for the third target, and wherein the combined number is determined by summing a number of partitions in the alpha population, a number of partitions in a population positive only for the first target, a number of partitions in a population positive only for the second target, and a number of partitions negative for all three targets.

24. The method of any of paragraphs 20 to 23, wherein the step of determining a level of the third target includes a step of calculating a concentration of the third target with a value for a total number of partitions in a combination of the alpha population, the beta population, a population positive only for the first target, a population positive only for the second target, and a population negative for all three targets.

25. The method of paragraph 24, wherein the step of calculating a concentration of the third target is performed with the value for a total number of partitions and (a) a value for a number of partitions in the beta population or (b) a value for a number of partitions negative for the third target.

26. The method of any of paragraphs 20 to 25, wherein the step of determining a number of partitions in the alpha population is performed in part with a value for a number of partitions negative for all three targets.

27. The method of paragraph 26, wherein the step of determining a number of partitions in the alpha population is performed with a value for a number of partitions positive only for the first target, a value for a number of partitions positive only for the second target, and a value for a number of partitions negative for all three targets.

28. The method of paragraph 27, wherein the step of determining a number of partitions in the alpha population includes a step of calculating a ratio including the value for a number of partitions negative for all three targets, the value for a number of partitions positive only for the first target, and the value for a number of partitions positive only for the second target.

29. The method of any of paragraphs 20 to 28, wherein the step of determining a level of the first target is performed with only a portion of the data that selectively excludes each partition positive for the second target and each partition positive for the third target, and wherein the step of determining a level of the second target is performed with only a portion of the data that selectively excludes each partition positive for the first target and each partition positive for the third target;

30. The method of any of paragraphs 20 to 29, wherein the same fluid volume includes reagents sufficient for amplification of each of the targets.

31. The method of any of paragraphs 20 to 30, wherein each partition includes one or more reporters collectively sensitive to amplification of each of the targets.

32. The method of paragraph 31, wherein the one or more reporters include at least one probe different probe for each of the targets.

33. The method of paragraph 31, wherein the one or more reporters include a generic reporter that is sensitive to amplification of each of the targets.

34. The method of any of paragraphs 20 to 33, wherein each of the targets is provided by copies of at least one genome, wherein one of the targets is a reference sequence having a known copy number in the at least one genome, and wherein another of the targets is a normal sequence from a gene of interest, further comprising a step of determining a copy number of the normal sequence in the at least one genome with a level of the normal sequence and a level of the reference sequence.

35. The method of paragraph 34, wherein still another of the targets is a variant sequence from the gene of interest.

36. The method of paragraph 35, wherein the normal sequence and the variant sequence overlap each other in the gene of interest to define a region of overlap, and wherein the variant sequence and the normal sequence differ by at least one nucleotide in the region of overlap.

37. The method of paragraph 35, wherein the first target is the reference sequence, wherein the second target is the variant sequence, and wherein the third target is the normal sequence.

38. The method of any of paragraphs 20 to 37, wherein the partitions include a first probe sensitive to amplification of the first target and labeled with a first luminophore, a second probe sensitive to amplification of the second target and labeled with the second luminophore different from the first luminophore, and a third probe sensitive to amplification of the third target and labeled with the first luminophore and the second luminophore.

39. The method of paragraph 38, wherein the third probe includes a probe labeled with the first luminophore and not the second luminophore and another probe labeled with the second luminophore and not the first luminophore.

40. The method of any of paragraphs 20 to 39, wherein the data are collected in no more than two optical channels representing wavelength regimes that are different from each other.

41. The method of any of paragraphs 20 to 40, wherein the data are collected from the plurality of partitions at about a same temperature.

42. The method of any of paragraphs 20 to 41, wherein the step of collecting data is performed after the step of amplifying has been completed.

43. The method of any of paragraphs 20 to 42, wherein the first target and the second target are not substantially linked to each other when the partitions are formed.

44. The method of any of paragraphs 20 to 43, wherein the second target and the third target are distinct sequences from a same gene.

45. The method of paragraph 44, wherein the second target is a variant sequence of the gene and the third target is a normal sequence of the gene, or vice versa.

46. The method of paragraph 45, wherein the normal sequence and the variant sequence overlap each other in the gene to define a region of overlap, and wherein the variant sequence and the normal sequence differ by at least one nucleotide in the region of overlap.

47. The method of any of paragraphs 44 to 46, wherein the gene is a cancer-related gene.

48. The method of any of paragraphs 20 to 47, further comprising a step of creating a plot of the data, wherein the alpha population at least partially overlaps the beta population in the plot of the data.

49. The method of paragraph 48, wherein each axis of the plot represents a different wavelength regime for detected light.

50. The method of paragraph 48, wherein only one axis of the plot represents detected light.

51. The method of any of paragraphs 20 to 50, wherein the first target is a reference sequence, further comprising a step of determining a copy number of the second target from the level of the first target and the level of the second target and a step of determining a copy number of the third target by from the level of the first target and the level of the third target.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a multiplexed digital assay, the method comprising:
    forming partitions each including a portion of a same sample comprising nucleic acid, the sample including a first target that is a reference sequence, a second target that is a variant sequence from a gene of interest, and a third target that is a normal sequence from the gene of interest, wherein each partition of only a subset of the partitions contains the first target and the second target, and wherein each partition of only a subset of the partitions contains the third target;
    amplifying the first target, the second target, and the third target in the partitions;
    collecting data from a plurality of the partitions for amplification of each of the targets, wherein partitions positive for both the first target and the second target are not distinguishable from partitions positive for only the third target;
    determining a level of the second target; and
    determining a copy number of the third target with a level of the first target and a level of the third target.

2. The method of claim 1, wherein the gene of interest is a cancer-related gene.

3. The method of claim 1, wherein the variant sequence and the normal sequence overlap each other in the gene of interest to define a region of overlap, and wherein the variant sequence and the normal sequence differ by at least one nucleotide in the region of overlap.

4. The method of claim 1, wherein, in the data collected, signals for an alpha population of partitions positive for each of the first and second targets have a range that overlaps corresponding signals for a beta population of partitions positive for only the third target.

5. The method of claim 4, further comprising a step of determining a level of the first target, wherein the steps of determining a level of the first target and determining a level of the second target are each performed with only a portion of the data that excludes the alpha population and the beta population.

6. The method of claim 5, wherein the step of determining a level of the first target is performed with values obtained from only a portion of the data that selectively excludes partitions positive for the second target and partitions positive for the third target, and wherein the step of determining a level of the second target is performed with values obtained from only a portion of the data that selectively excludes partitions positive for the first target and partitions positive for the third target.

7. The method of claim 5, further comprising a step of determining a level of the third target based at least in part on a value for a number of partitions in the alpha population.

8. The method of claim 1, wherein the data are collected in no more than two different optical channels.

9. The method of claim 1, wherein the sample includes copies of at least one genome that provides the targets, and wherein the reference has a known copy number in the at least one genome.

10. The method of claim 1, wherein the partitions include a first probe sensitive to amplification of the first target and labeled with a first luminophore, a second probe sensitive to amplification of the second target and labeled with a second luminophore different from the first luminophore, and a third probe sensitive to amplification of the third target and labeled with the first luminophore and the second luminophore.

11. The method of claim 10, wherein the third probe includes a probe labeled with the first luminophore and not the second luminophore and another probe labeled with the second luminophore and not the first luminophore.

12. The method of claim 1, wherein the data are collected from the plurality of partitions at about a same temperature.

13. The method of claim 1, further comprising a step of determining a copy number of the second target from the level of the first target and the level of the second target.

14. A method of performing a multiplexed digital assay, the method comprising:
  forming partitions each including a portion of a same fluid volume that contains a first target, a second target, and a third target from a nucleic acid sample, wherein each partition of only a subset of the partitions contains the first target and the second target, and wherein each partition of only a subset of the partitions contains the third target;
  amplifying the first target, the second target, and the third target in the partitions;
  collecting data from a plurality of the partitions for amplification of each of the targets, wherein in the data an alpha population of partitions each positive for both of the first and second targets at least partially overlaps a beta population of partitions positive for only the third target, such that partitions positive for only the third target are not distinguishable from partitions each positive for both the first target and the second target;
  determining a level of the first target and a level of the second target from only a portion of the data that excludes both the alpha population and the beta population;
  determining a number of partitions in the alpha population; and
  determining a level of the third target based in part on the number of partitions in the alpha population.

15. The method of claim 14, wherein the step of determining a level of the third target includes a step of calculating a number of partitions in the beta population based at least in part on the number of partitions in the alpha population.

16. The method of claim 14, wherein the step of determining a level of the first target is performed with only a portion of the data that selectively excludes each partition positive for the second target and each partition positive for the third target, and wherein the step of determining a level of the second target is performed with only a portion of the data that selectively excludes each partition positive for the first target and each partition positive for the third target.

17. The method of claim 14, wherein each of the targets is provided by copies of at least one genome, wherein one of the targets is a reference sequence having a known copy number in the at least one genome, wherein another of the targets is a normal sequence from a gene of interest, and wherein still another of the targets is a variant sequence from the gene of interest.

18. The method of claim 14, wherein the data are collected in no more than two optical channels representing wavelength regimes that are different from each other.

19. The method of claim 14, wherein the data are collected from the plurality of partitions at about a same temperature.

20. The method of claim 14, further comprising a step of creating a plot of the data, wherein the alpha population at least partially overlaps the beta population in the plot of the data.

* * * * *